United States Patent [19]

Fields, Jr. et al.

[11] Patent Number: 4,965,403

[45] Date of Patent: Oct. 23, 1990

[54] OXIDATION/DEALKYLATION PROCESS

[75] Inventors: Donald L. Fields, Jr., Manchester; William H. Miller, Glendale; Mitchell J. Pulwer, St. Louis, all of Mo.

[73] Assignee: Monsanto Company, St. Louis, Mo.

[21] Appl. No.: 267,870

[22] Filed: Nov. 7, 1988

[51] Int. Cl.$^5$ .............................................. C07F 9/38
[52] U.S. Cl. ..................................................... 562/17
[58] Field of Search .................... 260/502.5 F; 562/17

[56] References Cited

U.S. PATENT DOCUMENTS

| | | | |
|---|---|---|---|
| 2,384,817 | 9/1945 | Chitwood | 562/526 |
| 3,969,398 | 7/1976 | Hershman | 260/502.5 |
| 4,442,041 | 4/1984 | Subrmanian | 260/502.5 F |
| 4,587,061 | 5/1986 | Miller et al. | 260/502.5 F |

FOREIGN PATENT DOCUMENTS

| | | |
|---|---|---|
| 55695 | 7/1982 | European Pat. Off. |
| 2363634 | 6/1974 | Fed. Rep. of Germany |

OTHER PUBLICATIONS

Marahashi, et al, *J. Amer. Chemical Soc.* 101, 7429 1979.

Primary Examiner—J. E. Evans
Attorney, Agent, or Firm—Frank D. Shearin

[57] ABSTRACT

There is disclosed a process for producing the alkali metal salts of N-phosphonomethylglycine which comprises heating to an elevated temperature a di-alkali metal salt of N-alkyl-N-(2-hydroxyethyl)aminomethylphosphonic acid.

11 Claims, No Drawings

OXIDATION/DEALKYLATION PROCESS

BACKGROUND OF THE INVENTION

This invention relates to a process for preparing N-phosphonomethylglycine by the simultaneous oxidation and dealkylation of an N-alkyl-N-(2-hydroxyethyl)aminomethylphosphonic acid. More particularly, the invention relates to a relatively simple method whereby N-phosphonomethylglycine is produced in high yield and yet relatively free of reaction by-products.

N-Phosphonomethylglycine, known also by its common name glyphosate, is a highly effective and commercially important phytotoxicant useful in controlling a large variety of weeds and crops. It is applied to the foliage of a very broad spectrum of perennial and annual grasses and broad-leafed plants to achieve the desired control. Industrial uses include control of weeds along roadsides, waterways, transmission lines, in storage areas, and in other nonagricultural areas. Usually glyphosate is formulated into herbicidal compositions in the form of its various salts which retain the anionic form of glyphosate in solution, preferably in water.

Because of its commercial importance, many processes for making glyphosate have been published. One process for the manufacture of glyphosate is described by Gaertner in U.S. Pat. No. 3,927,080. Gaertner describes the production of glyphosate wherein N-t-butyl-N-phosphonomethylglycine or its esters are hydrolyzed under acidic conditions.

In European Patent No. 0,055,695, there is disclosed a process for splitting for a substituent group from the nitrogen atom of an N-substituted N-phosphonomethylglycine by catalytic hydrogenolysis. The N-substituent is described as a 1-arylalkyl group suitable for hydrogenolytic cleavage. The hydrogenolytic process is carried out in the presence of a catalyst, such as platinum or palladium on barium sulfate. The chemistry of the carbon/nitrogen bond of amines has been the subject of extensive study in recent years. For example, Murahashi and Watanabe disclosed the metal catalyzed reaction of tertiary amines with water in an article entitled "Palladium Catalyzed Hydrolysis of Tertiary Amines with Water" published in the *Journal of the American Chemical Society*, 101, 7429 (1979). In this publication it was reported that catalytic oxidation of tertiary amines proceeded generally and efficiently with palladium catalysts to provide secondary amines and carbonyl compounds.

Another process for the manufacture of glyphosate is described by Hershman in U.S. Pat. No. 3,969,398. In said process N-phosphonomethyliminodiacetic acid is catalystically oxidized to produce glyphosate.

A process to produce glyphosate using a metal catalyst is described in U.S. Pat. No. 4,442,041. This patent teaches a process for the conversion of the diethyl ester of [bis(2-hydroxyethyl)amino]methylphosphonic acid into N-phosphonomethylglycine in the presence of catalysts such as zinc oxide or cadmium oxide. The process described comprises the steps of:

(1) reacting the diethyl ester [bis(2-hydroxyethyl)amino]methylphosphonic acid in an oxygen free atmosphere with an alkali metal hydroxide selected from the group consisting of sodium hydroxide and potassium hydroxide, in the presence of water as solvent and a catalyst selected from the group consisting of zinc oxide and cadmium oxide at a high temperature and pressure for a sufficient period of time to cause the reaction to go to completion, and, (2) acidifying the product formed.

The process results in only a 33.1% yield of glyphosate in the one example described. This poor yield appears to be largely due to the formation of by-products by competing reactions. Oxidation of both 2-hydroxyethyl side chains would give N-phosphonomethyliminodiacetic acid (NP-IDA). In our studies this indeed seems to be the dominant component of the mixture produced by the process of the prior art as illustrated in example 12 of this specification. On the other hand dealkylation of both these side chains would yield aminomethylphosphonic acid. By contrast, the production of glyphosate requires the dealkylation of one side chain along with the oxidation of the other. Thus the yield of glyphosate appears to depend on the balance between the competing reactions.

A process has now been discovered by which substituted or unsubstituted N-alkyl groups can be cleared from N-alkyl-(2-hydroxyethyl)aminomethylphosphonic acids (hereinafter called NNAMP acids) while the 2-hydroxyethyl group is simultaneously oxidized under alkaline conditions in the absence of any catalyst.

In surprising contrast to the teaching of the U.S. Pat. No. 4,442,041 it has now been shown that if the heavy metal catalyst described is omitted, the yield of glyphosate is considerably increased over that described, even when the reaction is operated under otherwise equivalent conditions. Example 12 shows a detailed examination of the disodium salt of [bis(2-hydroxyethyl)amino]methylphosphonic acid under catalytic and non-catalytic conditions and demonstrates the substantial increase in glyphosate yields under the non-catalytic conditions. The uncatalyzed process was found to give consistent yields of N-phosphonomethylglycine in excess of 50%, as opposed to the maximum 33% yield of N-phosphonomethylglycine reported in U.S. Pat. No. 4,442,041.

In addition to the improved yields when no catalyst is used, there is also a distinct environmental (as well as economic) advantage in not using such catalysts. In such a reaction some catalyst is inevitably entrained with the waste stream. The complete removal of such heavy metals is not easily accomplished and they can often find their way into the environment as pollutants.

DESCRIPTION OF THE INVENTION

The present invention provides a process for producing the alkali metal salts of N-phosphonomethylglycine which comprises heating to a temperature of above about 200° C., a di-alkali metal salt of an N-alkyl-N-(2-hydroxyethyl)-aminomethylphosphonic acid wherein the N-alkyl group is represented by the formula

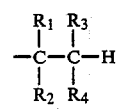

wherein $R_1$, $R_2$, $R_3$, and $R_4$ are independently selected from the group consisting of hydrogen, $C_{1-6}$ alkyl, benzyl, aryl, substituted aryl, and $R_3$ and $R_4$ can also be independently selected from halogens, OH, $C_{1-4}$ alkoxy, aryloxy, SH, $C_{1-4}$ alkylthio, arylthio, $-NR_5R_6$ wherein $R_5$ and $R_6$ are independently selected from hydrogen, $C_{1-4}$ alkyl, and aryl provided that $R_3$ and $R_4$ cannot both be —OH, or —SH.

One characteristic of the reaction of the present invention is the production of an olefin by-product. When one of the other beta substituents is a hetero atom, such as nitrogen, oxygen, or sulfur, the olefin by-product may be transient and removed in a different form.

The reaction comprises the dealkylation of the starting material and the simultaneous oxidation of the 2-hydroxyethyl group to the corresponding carboxylic acid group. It is understood that the 2-hydroxyethyl group can be generated in situ by hydrolysis of a suitable substituent.

The term "halogen" as employed herein includes all members of the class, i.e., chlorine, fluorine, bromine, and iodine.

The term aryl as employed herein includes groups such as phenyl, naphthyl, biphenyl, or phenyl, naphthyl, or biphenyl substituted with from 1 to 3 substituents independently selected from the class consisting of lower alkyl, lower alkoxy, methylenedioxy, halogen, cyano, nitro, $C_{1-4}$ haloalkyl, and alkylthio.

Illustrative of the substituted phenyl groups are mono-substituted phenyl wherein the substituent is in the ortho, meta, or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl and the like, and the di- and tri-substituted phenyl groups wherein the substituents are the same or different and are located in the 2, 3, 4, 5, or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, diethyl-thiophenyl, trimethylphenyl, trichlorophenyl, tributylphenyl, ethyldichlorophenyl and the like.

Groups representative of a substituted naphthyl group include methylnaphthyl, nitronaphthyl, bromonaphthyl, dimethylnaphthyl, difluoronaphthyl, trimethylnaphthyl and the like.

Groups representative of substituted biphenyl groups include methylbiphenyl, nitrobiphenyl, bromobiphenyl, dimethylbiphenyl, difluorobiphenyl, trimethylbiphenyl and the like.

The term aryloxy as employed herein includes the above-mentioned aryl groups when joined by an oxygen linkage in the above-described formula, and similarly the term arylthio as employed herein includes the above-mentioned aryl groups when joined by a sulfur linkage to the above-described formula.

The term alkylthio as employed herein includes the above-described alkyl groups when joined to the above-described formula by a sulfur linkage.

Typical examples of —$NR_5R_6$ included within the scope of this invention are dimethylamine, methylethylamino, phenylmethylamino, diethylamino and the like.

A particularly preferred embodiment of an NNAMP is one in which the "N-alkyl" group is a 2-hydroxyethyl group. As is discussed above the process of the invention permits the production of a very much greater proportion of glyphosate than is obtainable using the process of U.S. Pat. No. 4,442,041. This is demonstrated in detail in Example 12 below.

The molar ratio of alkali metal base to NNAMP acid equivalent in the reaction mixture is generally in the range of from about 3 to 12 or more moles of alkali metal base to 1 mole of the NNAMP. In a preferred embodiment of this invention, the NNAMP salt is formed in situ and the molar ratio of alkali metal base to the NNAMP acid is in the range of about 4 to 1 to 10 to 1 and preferably from about 4 to 1 to 6 to 1. Correspondingly reduced ratios are appropriate if the preformed salt is used, respectively.

The di-alkali metal salt of the NNAMP can be provided by preforming the salt by combining the NNAMP with an appropriate amount of base. The preformed salt may then be added to water or an aqueous base for use in this invention. Alternatively, the desired alkali metal salt may be formed in situ by combining an NNAMP acid or a hydrolyzable derivative of the NNAMP acid with an appropriate amount of an alkali metal base.

The salts of the NNAMP employed are the alkali metal salts. Preferably, the sodium salt is employed in the process of this invention.

As noted above, the alkali metal salts of an NNAMP employed in the process of this invention are derived from an NNAMP or a hydrolyzable derivative of an NNAMP. Because the process of this invention is performed at elevated temperatures under relatively strongly basic conditions, many different hydrolyzable NNAMP derivatives can be employed. Such derivatives can be employed because when combined with an aqueous base in accordance with this invention, hydrolysis takes place to form the desired alkali metal salt. Examples of such NNAMP derivatives are esters, amides, strong acid salts, thioesters, and mixtures thereof. Typical examples of said hydrolyzable derivatives of NNAMP are known in the prior art as, for example, U.S. Pat. No. 3,799,758 to Franz, which patent is hereby incorporated by reference.

The salt of N-phosphonomethylglycine produced by the process of this invention is readily converted to the acid, N-phosphonomethylglycine, as for example, by acidification with mineral acids as is well known in the art.

While the process of this invention proceeds throughout a wide range of temperatures, typically in the range of above about 200° C., it is preferred to operate the process of this invention in the range of from about 250° C. to about 350° C. Generally, the upper limit of the temperature range in the operation of the process of this invention is dependent upon the thermal stability of materials employed in the reaction mixture.

In the process of this invention, water is retained in the reaction mixture by appropriate means, typically by maintaining the pressure over the reaction mixture in excess of the vapor pressure of water at the temperature of the reaction. In a preferred process, this is done by reaction in an autoclave.

The NNAMP employed in the process of this invention in the form of an alkali metal salt is obtained by known processes. See, for example, U.S. Pat. No. 3,288,846 to Irani et al and Moedritzer et al, *J. Org. Chem.*, 31, 1603 (1966). The reactions described therein are easily adapted to provide the tertiary amines employed in the process of this invention.

DESCRIPTION OF PREFERRED EMBODIMENT

The following examples serve to illustrate the process of this invention and are not intended to limit the invention in any way.

EXAMPLE 1

To a 100 ml Monel autoclave were charged 2.17 g (11.0 mmol) of N-(2-hydroxyethyl)-N-isopropylaminomethylphosphonic acid and 13.1 g (165 mmol) of a 50.3% solution of NaOH to give a thick paste. The vessel was sealed and heated to 250° C. After little visible reaction during a two hour period at this temperature, the temperature was raised to 300° C. and held there for three hours. During this time the internal pressure of the reaction vessel rose from $1.7 \times 10^6$ $N/M^2$ to $3.4 \times 10^6$ $N/M^2$ as a result of the liberation of gases in the course of the reaction. The vessel was cooled to room temperature and the residual internal pressure was released. The reaction mixture consisted of a thick slurry of white solids. The mixture was diluted with 10 ml of water and neutralized by the addition of 165 mmol of HCl. The resulting solution was concentrated to dryness. The residue was taken up in conc. HCl and the precipitated NaCl was filtered off. The remaining filtrate was concentrated and then purified by ion exchange chromatography (Dowex 50×8-400). Isolated from the chromatography were 0.85 g (45%) of N-phosphonomethylglycine (NMR, $D_2O$) δ 4.10 (s,2H), 3.23 (d,J=12 Hz, 2H); 0.26 g (11%) of N-isopropyl-Nphosphonomethylglycine (NMR, $D_2O$) δ 4.13 (s,2H), 3.96 (Sept., J=7 Hz, 1H), 3.40 (d,J=12 Hz, 2H), 1.35 (d,J=7 Hz, 6H); 0.26 g (22%) of aminomethylphosphonic acid (NMR, $D_2O$) δ 3.08 (d,J=12 Hz, 2H); and 0.36 g (22%) of N-isopropylaminomethylphosphonic acid (NMR, $D_2O$) δ 3.50 (Sept., J=7 Hz, 1H), 3.13 (d,J=12 Hz, 2H), 1.33 (d,J=7 Hz, 6H). All yields were based upon the amount of starting substrate.

EXAMPLE 2

In a 100 ml Monel autoclave were mixed 2.30 g (11.7 mmol) of N-(2-hydroxyethyl)-N-isopropylaminomethylphosphonic acid and 3.73 g (93.0 mmol) of dry, powdered NaOH. The reagents were mixed together well. The reaction vessel was flushed with $N_2$, and the mixture was heated to 315° C. for three hours. During the heating period at 315° C. the internal pressure in the vessel rose from $5 \times 10^5 N/M^2$ to $1.3 \times 10^6 N/M^2$. At the end of the heating period the excess pressure that was generated was released and 8 ml of water were introduced. The temperature of the reaction was maintained at 300° C. for three hours while the internal pressure rose from $3.1 \times 10^6 N/M^2$ to $3.9 \times 10^6 N/M^2$. The vessel was then cooled to room temperature and the residual pressure was released. The reaction mixture was diluted with water and neutralized with 93 mmol of HCl. This solution was concentrated to dryness. The residue was taken up in conc. HCl and the precipitated NaCl was filtered off. The filtrate was concentrated and purified by ion exchange chromatography (Dowex 50×8-400), to yield 1.03 g (52.0%) of N-phosphonomethylglycine and 0.32 g (13.0%) of N-isopropyl-N-phosphonomethylglycine

EXAMPLE 3

To a 100 ml Monel autoclave were charged 2.08 g (11.4 mmol) of N-ethyl-N-(2-hydroxyethyl)-aminomethylphosphonic acid and 3.63 g (91 mmol) of dry, powdered NaOH. The two powders were intimately mixed. To this mixture 1 ml of water was added and mixed until the dampness was evenly distributed through the mass. The reaction vessel was then flushed with $N_2$, sealed and heated to 315° C. for two and a half hours. When the vessel had reached 315° C. an internal pressure of $2.2 \times 10^6$ $N/M^2$ had been established. By the end of the heating period the pressure had risen to $3.5 \times 10^6 N/M^2$. The excess pressure generated to this point was released and an additional 9 ml of $H_2O$ were introduced. The reaction temperature was adjusted to 300° C. which produced an internal pressure of $4.3 \times 10^6$ $N/M^2$. After five hours of heating at 300° C., the internal pressure had reached $4.6 \times 10^6$ $N/M^2$. The reaction was allowed to cool to room temperature at which point the residual pressure was released. The reaction mixture was diluted with water and neutralized with 91 mmol of HCl. The solution was stripped to dryness. The residue was taken up in conc. HCl and the precipitated NaCl was filtered off. The filtrate was concentrated and purified by ion exchange chromatography to yield 0.38 g (20%) of N-phosphonomethylglycine based on the original substrate.

EXAMPLE 4

To a 100 ml Monel autoclave were added 1.88 g (11.4 mmol) of 4-ethyl-2-hydroxy-2-oxo-tetrahydro-4H-1,4,2-oxazaphosphorine and 3.63 g (91 mmol) of dry, powdered NaOH. The powders were mixed and crushed together well. To this mixture was added 1 ml of water and the combination was thoroughly mixed to give a sticky solid. The vessel was flushed with $N_2$, sealed and heated to 315° C. At this temperature an autogenous pressure of $2.2 \times 10^6 N/M^2$ had developed. The temperature was maintained at 315° C. for three hours. During this period pressure that was generated by the reaction was carefully vented to maintain the level at about $2.4 \times 10^6 N/M^2$. An additional 7 ml of $H_2O$ was introduced and the reaction was heated at 300° C. (initial pressure of $3.1 \times 10^6 N/M^2$). During the three hour heating period at 300° C. the pressure rose to $3.9 \times 10^6 N/M^2$. After cooling to room temperature, the residual pressure was released. The reaction mixture was diluted with water, neutralized with 91 mmol of HCl, and concentrated to dryness. The residue was taken up in conc. HCl and precipitated NaCl was filtered away. The filtrate was concentrated and then purified by ion exchange chromatography (Dowex 40×8-400) to yield 0.59 g (30.7%) of N-phosphonomethylglycine.

EXAMPLE 5

In a 100 ml Monel autoclave reactor were placed [bis(2-hydroxyethyl)amino]methylphosphonic acid (4.0 g, 0.02 mol), and a 40% solution of sodium hydroxide (8.0 g, 0.2 mol) and water (12 g). The autoclave was purged with nitrogen and the mixture was heated at 270° C. for 60 minutes. The cooled reaction mixture was diluted with water, acidified using HCl and the water was evaporated to give an oily solid. The mixture was stirred in 37% HCl (100 ml) for 5 minutes and then filtered to remove precipitated NaCl. Evaporation of the solvent and separation by medium pressure liquid chromatography on Dowex 50×8-400 ion exchange resin gave a mixture of N-phosphonomethyliminodiacetic 412 acid (1.7 g, 37.3%), N-phosphonomethylglycine (1.8 g, 53.5%) and aminomethylphosphonic acid (0.2 g, 8.9%). The compounds were identified by H NMR spectra as compared to pure standards; N-phosphonomethyliminodiacetic acid: H NMR ($D_2O$) δ 4.2 (s,4H), 3.5 (d,J=12.0 Hz, 2H) N-phosphonomethylglycine: $^1$H NMR ($D_2O$) 3.8 (s,2H), 3.2 (d,J=12.0 Hz 2H).

Aminomethylphosphonic acid: H NMR (D₂O) 3.1 (d,J=12.0 Hz, 2H).

In the following Examples 6 to 11 the procedure of Example 5 was followed except where otherwise indicated.

EXAMPLE 6

Following the procedure described in Example 5, 2-hydroxy-2-oxo-tetrahydro-4H-1,4,2-oxazaphosphorine-4-ethanol, (3.0 g, 0.016 mol) was heated in a 40% solution of sodium hydroxide (6.1 g, 0.15 mol) and water (9.0 g) at 270° C. for 120 minutes. Work-up gave N-phosphonomethyliminodiacetic acid (1.0 g, 29.5%), N-phosphonomethylglycine (1.4 g, 52.9%) and aminomethylphosphonic acid (0.24 g, 13.6%).

EXAMPLE 7

The disodium salt of [bis(2hydroxyethyl)amino]methylphosphonic acid monohydrate (10.0 g, 0.04 mol) was reacted in a 40% solution of sodium hydroxide (6.4 g, 0.16 mol) and water (10.0 g) at 270° C. for 130 minutes. The product mixture gave N-phosphonomethyliminodiacetic acid (2.76 g, 33.2%), N-phosphonomethylglycine (2.68 g, 51.2%) and aminomethylphosphonic acid (0.56 g, 10.2%).

EXAMPLE 8

The disodium salt of [bis(2hydroxyethyl)amino]methylphosphonic acid monohydrate (4.0 g, 0.016 mol) was heated with 85% potassium hydroxide (15.0 g, 0.23 mol) at 250° C. for 75 minutes. Product isolation gave N-phosphonomethylglycine (0.31 g, 12.6%) and aminomethylphosphonic acid (1.0 g, 60.0%).

EXAMPLE 9

The procedure of Example 5 was followed in heating the disodium salt of [bis(2hydroxyethyl)amino]methylphosphonic acid trihydrate (2.0 g, 0.007 mol) in a 20% solution of potassium hydroxide (1.5 g, 0.02 mol) and sodium hydroxide (1.1 g, 0.03 mol) in water (10.0 g) at 250° C. for 60 minutes. Product isolation gave N-phosphonomethylglycine (0.57 g, 50.4%) and aminomethylphosphonic acid (0.14 g, 18.7%).

EXAMPLE 10

The disodium salt of [bis(2hydroxyethyl)amino]merhylphosphonic acid (1.6 g, 0.006 mol) was heated in a 11.5% solution of sodium hydroxide (1.5 g, 0.04 mol) in water (10.0 g) at 270° C. for 90 minutes. Work-up gave N-phosphonomethylglycine (0.56 g, 51.4%) and aminomethylphosphonic acid (0.30 g, 41.5%).

EXAMPLE 11

The disodium salt of [bis(2- (hydroxyethyl)amino]methylphosphonic acid trihydrate (2.0 g, 0.007 mol) in a 40% solution of potassium hydroxide (5.0 g, 0.8 mol) and sodium hydroxide (5.0 g, 0.125 mol) in water (15.0 g) was heated at 230° C. for 60 minutes. The product mixture contained N-phosphonomethyliminodiacetic acid (0.30 g, 19.6%), N-phosphonomethylglycine (0.24 g, 21.1%) and aminomethylphosphonic acid (0.17 g, 22.7%).

EXAMPLE 12

This Example compares the performance of the process of the invention with that obtained using heavy metal catalysts in the same reaction. The results are presented in Table 1 below. The procedure used was essentially that of Example 5 using the disodium salt of [bis(2-hydroxyethyl)amino]methylphosphonic acid as the organic reactant except where noted.

TABLE 1

| Catalyst | NaOH Concentr. % | Time (Min.) | Temp ° C. | Product (%) Glyphosate | Product (%) NP-IDA* |
|---|---|---|---|---|---|
| CdO | 40 | 120 | 260 | 28.6 | 68.1 |
| ZnO | 40 | 150 | 270 | 13.0 | 64.6 |
| CuO | 40 | 60 | 270 | 36.0 | 47.7 |
| PtO₂ | 40 | 240 | 260 | 31.5 | 43.7 |
| **Cu SO₄ | 40 | 60 | 270 | 28.5 | 53.7 |
| 5% Pt/C | 40 | 240 | 260 | 23.0 | 50.9 |
| None(Ex 5) | 40 | 60 | 270 | 53.5 | 37.3 |
| None(Ex 7) | 40 | 130 | 270 | 51.2 | 33.2 |

*N-phosphonomethyliminodiacetic acid
**Organic reactant = [bis(2-hydroxyethyl)amino]-methylphosphonic acid.

The above results show clearly that the use of the heavy metal catalyst clearly favors the oxidation of the -ethanol group to the -acetic acid group. Since the oxidized group cannot be removed (dealkylation) by the reaction with alkali, the yields are obviously significantly reduced in the presence of such catalysts.

What is claimed is:

1. A process for producing the alkali metal salts of N-phosphonomethylglycine which comprises reacting, in the absence of a catalyst, an alkali metal hydroxide at a temperature of above about 200° C., with a di-alkali metal salt of an N-alkyl-N-(2-hydroxyethyl)aminomethylphosphionic acid wherein the N-alkyl group is represented by the formula:

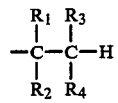

wherein $R_1$, $R_2$, $R_3$, and $R_4$ are independently selected from the group consisting of hydrogen, $C_{1-6}$ alkyl, benzyl, aryl, substituted aryl, and $R_3$ and $R_4$ can also be independently selected from halogens, OH, $C_{1-4}$ alkoxy, aryloxy, SH, $C_{1-4}$ alkylthio, arylthio, —$NR_5R_6$ wherein $R_5$ and $R_6$ are independently selected from hydrogen, $C_{1-4}$ alkyl, and aryl provided that $R_3$ and $R_4$ cannot both be —OH, or —SH.

2. The process of claim 1 additionally containing the step of acidifying the salt of N-phosphonomethylglycine to provide N-phosphonomethylglycine.

3. The process of claim 1 wherein the the temperature is in the range of from about 250° C. to about 350° C.

4. The process of claim 1 wherein the alkali metal hydroxide base is selected from the group consisting of sodium hydroxide, potassium hydroxide, and lithium hydroxide.

5. The process of claim 1 wherein the dialkali metal salt is formed in situ.

6. The process of claim 1 wherein the N-alkyl group is isopropyl.

7. The process of claim 1 wherein the salt is formed in situ by reacting an alkali metal hydroxide and an N-alkyl-N-(2-hydroxyethyl)aminomethylphosphonic acid in a molar ratio of from about 4 to 1 to about 10 to 1, respectively.

8. The process of claim 7 wherein the N-alkyl group is isopropyl.

9. The process of claim 7 wherein the base is sodium hydroxide.

10. The process of claim 7 wherein the N-alkyl group is ethyl.

11. The process of claim 7 wherein the N-alkyl group is 2-hydroxyethyl.